(12) United States Patent
Nguyen et al.

(10) Patent No.: US 7,049,151 B2
(45) Date of Patent: May 23, 2006

(54) ASSAY SYSTEM FOR SIMULTANEOUS DETECTION AND MEASUREMENT OF MULTIPLE MODIFIED CELLULAR PROTEINS

(75) Inventors: Quan Nguyen, Pleasant Hill, CA (US); Yong Song, San Pablo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 526 days.

(21) Appl. No.: 10/092,926

(22) Filed: Mar. 6, 2002
(Under 37 CFR 1.47)

(65) Prior Publication Data

US 2003/0040020 A1     Feb. 27, 2003

Related U.S. Application Data

(60) Provisional application No. 60/274,130, filed on Mar. 7, 2001.

(51) Int. Cl.
*G01N 33/543* (2006.01)

(52) U.S. Cl. ............... 436/518; 436/523; 436/524; 435/7.1; 435/7.92; 435/973

(58) Field of Classification Search .......... 435/7.1, 435/7.92–7.94, 962, 967, 973, 9.92; 436/501, 436/518, 523, 524, 164
See application file for complete search history.

(56) References Cited

U.S. PATENT DOCUMENTS

| | | | |
|---|---|---|---|
| 4,639,425 A | | 1/1987 | Baier |
| 4,647,654 A | | 3/1987 | Knowles et al. |
| 4,658,022 A | | 4/1987 | Knowles et al. |
| 4,891,319 A | * | 1/1990 | Roser .................. 435/188 |
| 5,981,180 A | | 11/1999 | Chandler et al. |
| 6,197,599 B1 | | 3/2001 | Chin et al. |
| 6,329,209 B1 | | 12/2001 | Wagner et al. |
| 2003/0153014 A1 | * | 8/2003 | Shen et al. ............ 435/7.9 |

FOREIGN PATENT DOCUMENTS

WO    WO 00/16101    3/2000

OTHER PUBLICATIONS

Bayer et al., Immunoassay, edited by Diamandis et al.,, Chapter 11, The Avidin-Biotin System, p. 237-267, 1996.*
Johannsen, M. et al. "Native extraction of phosphotyrosine-containing proteins: Requirement of tyrosine kinase inhibitors to obtain specific phosphorylation signals," *Analytical Biochem.* 2000, pp. 242-245, vol. 279.
Strahl, B.D. and Allis, D. "The language of convalent histone modifications," *Nature* Jan. 6, 2000,pp. 41-45, vol. 403.
Tani, A. et al. "Development of EIA systems for active-form MAP kinase," *J. Immunological Methods* 2000, pp. 87-97, vol. 238.

* cited by examiner

*Primary Examiner*—Long V. Le
*Assistant Examiner*—Gary W. Counts
(74) *Attorney, Agent, or Firm*—Townsend and Townsend and Crew LLP

(57) ABSTRACT

A method and kit for simultaneous detection and/or determination of a plurality of modified proteins in a sample. The method comprises: a) contacting the sample under mild protein denaturation conditions with a plurality of first antibodies capable of binding to a specific target protein, the first antibodies being immobilized on solid support material, each first antibody being differentiable from others by a differentiation parameter, whereby the first antibodies bind to respective target proteins present in the sample; b) removing unbound materials from the locus of the first antibodies; c) contacting the materials from step (b) with one or more second antibodies, each of which is specific to a class or subclass of modified proteins or with a plurality of second antibodies, each of which is specific to a modified protein, so as to bind the second antibody or antibodies to modified proteins in the sample; and d) detecting and/or determining a plurality of modified proteins in the sample. The kit comprises a plurality of primary antibodies immobilized on solid support material, one or more buffers for lysing and for washing cellular material samples to be assayed, an assay buffer for conducting the assay, the buffer containing a sulfate or sulfonate detergent, and one or more second antibodies specific to the modified proteins.

24 Claims, 1 Drawing Sheet

ASSAY SYSTEM FOR SIMULTANEOUS DETECTION AND MEASUREMENT OF MULTIPLE MODIFIED CELLULAR PROTEINS

CROSS-REFERENCE TO RELATED APPLICATIONS

This application claims priority of U.S. provisional application No. 60/274,130 filed Mar. 7, 2001.

BACKGROUND AND PRIOR ART

This invention relates to improvements in processes for conducting "sandwich" assays of proteins and, in particular to an improved method for simultaneously detecting and/or determining, a plurality of modified proteins, especially modified cellular proteins, in a sample. In a typical "sandwich" assay for proteins, a sample (generally a biological fluid or cell extract) comprising a mixture of materials, including one or more proteins, is contacted with a series of microparticles or beads associated with antibodies that bind to the respective target proteins. Each combination of microparticles with a particular antibody has a feature, for instance color, that can distinguish it from the others. After washing away unbound materials, the microparticles, now containing proteins bound to the antibodies, are contacted with a second antibody that binds specifically to a particular protein to be detected. The second antibody typically includes a means for its detection, such as a fluorescent marker. The target protein is detected, and the quantity determined, by means suitable to the situation (e.g. scanning for fluorescence).

Most cellular proteins require modifications in order to transfer from their silent state to the active form. Such modifications include phosphorylation (for instance, on tyrosine, threonine and/or serine residues), glycosylation (on membrane proteins), and acetylation, prenylation and methylation (on lysine residues). Detection and measurement of such modified proteins, as currently carried out, is limited to processes that involve multiple steps but that can determine only a single modified protein in each assay. For instance, to investigate phosphorylation of proteins, current procedures use $^{32}$P-labeled inorganic phosphate in combination with immunoprecipitation and SDS-PAGE autoradiography or Western blot analyses specific for the phosphorylated form of the target protein. However Western blot processes for this purpose are slow and time-consuming and can only determine one analyte at a time.

A method for simultaneously detecting and, if desired, determining, two or more modified proteins in a sample, in a single operation, would be desirable.

SUMMARY OF THE INVENTION

This invention provides a method and kit for simultaneous detection and, if desired, quantitative determination, of a plurality of modified proteins in a given biological sample. These methods and kits are considered to be a satisfactory replacement for Western Blot determination of modified proteins.

In one aspect the invention comprises a method for simultaneous detection and/or determination of a plurality of modified proteins in a sample, comprising:
 a) contacting the sample under mild protein denaturation conditions with a plurality of first antibodies capable of binding to a specific target protein, the first antibodies being immobilized on solid support material, each first antibody being differentiable from others by a differentiation parameter, whereby the first antibodies bind to respective target proteins present in the sample;
 b) removing unbound materials from the locus of the first antibodies;
 c) contacting the materials from step (b) with one or more second antibodies, each of which is specific to a class or subclass of modified proteins or with a plurality of second antibodies, each of which is specific to a modified protein, so as to bind the second antibody or antibodies to modified proteins in the sample; and
 d) detecting and/or determining a plurality of modified proteins in the sample.

In another aspect, the invention involves a kit for carrying out such procedures, comprising
 (a) a plurality of first antibodies each capable of binding to a specific target protein, each first antibody being immobilized on a solid support material and each first antibody being differentiable from others by a differentiation parameter;
 (b) one or more buffers for lysing and for washing cellular material samples to be assayed
 (c) an assay buffer for conducting the assay, said buffer containing from about 1–10 mM of a sulfate or sulfonate detergent; and
 (d) one or more second antibodies specific to classes or subclasses of modified proteins or to specific individual modified proteins.

In yet another aspect, this invention involves a process for denaturation of modified proteins in an overall process for simultaneously analyzing a sample for a plurality of modified proteins, comprising contacting the sample with a sulfate or sulfonate detergent, preferably in a concentration of about 1–10 mM, at a temperature of between about 4 and about 37° C., and for a time of from about 2 to about 72 hours.

DETAILED DESCRIPTION OF THE INVENTION

Figure 1:
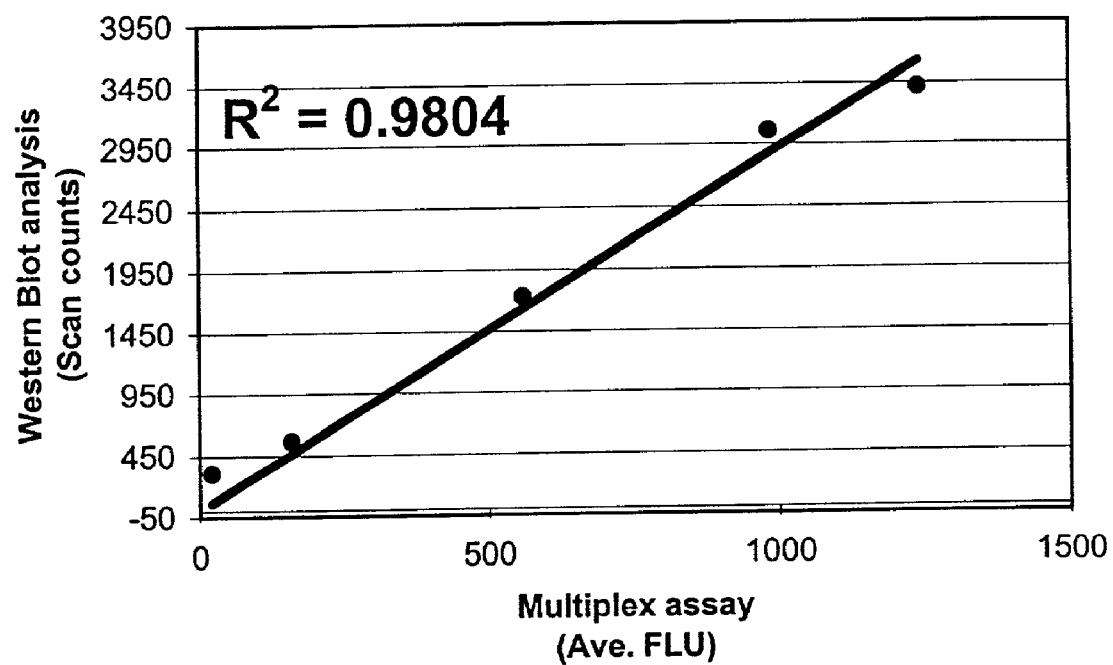
FIG. 1 depicts a comparison of analyses for the modified protein phospho-Erk2 using a method according to this invention and a Western blot analysis.

In carrying out the process of this invention, a sample of material is selected for analysis. The material in general is a biological fluid or cell extract, for instance, a cell lysate. The lysate may be obtained from various sources, including tissue culture cells, cells extracted from blood, or in vivo solid tissue samples. The lysate is contacted, under mild protein denaturation conditions, with a plurality of primary antibodies that are specific to the non-modified portion of the target proteins, i.e. proteins whose presence and/or quantity in the sample is to be detected or determined.

The primary antibodies are immobilized on a solid support material, each primary antibody being differentiable from others by a differentiation parameter. The solid support material may be a plurality of beads or other particles that are differentiable, and to which the antibodies are immobilized, for example via conjugation. Alternatively, the antibodies may be immobilized on a solid substance or device such as a microchip, plate (e.g. a 96-well plate) or slide.

For particulate supports, the capability to distinguish between combinations of particles with different antibodies (and thus between different antibodies) is accomplished by providing a plurality of particles of different types and immobilizing each primary antibody on particles of one type. That is, the particles may be divided into subsets, with each subset being distinguishable from other subsets according to a particular property, characteristic or characteristics. Each such subset is conjugated to a different primary antibody; thus each combination of particles with a particular antibody is distinguishable from combinations of particles with other antibodies. For example, the particles may be divided into subsets where each subset is capable of being distinguished by a specific color or emission spectra, which may be provided by the presence of a fluorochrome or combinations of fluorochromes incorporated within or on it, for example, as described in U.S. Pat. No. 5,981,180. The coupling of the antibodies to the beads or particles is accomplished by covalent coupling or adsorption methods well known to those familiar with the art and described in the patent and scientific literature (see, for instance, Immunochemistry of Solid-Phase Immunoassay, John E. Butler, CRC Press, 1991 and Immobilized Enzymes, Antigens, Antibodies, and Peptides, edited by Howard H. Weetall, Marcel Dekker, Inc. New York, 1975).

The particles themselves are typically spherical (i.e., "beads" or "microspheres"), with either a rough or a smooth surface, and are prepared as known in the art. They are made of various materials, usually non-porous glass, polystyrene, latex or other polymeric materials, and are generally 0.05 micron to 90 micron diameter, preferably 0.5 to 10 micron in diameter, with densities ranging from about 1 to 2 g/mL, preferably close to the density of water.

Once the combinations of primary antibodies and particle subsets are made, the subsets are combined for use in the assay procedure and/or kits of the invention.

If solid supports other than particles are used, for instance, glass, polymeric or silica chips, plates, slides, etc., the primary antibodies are immobilized on the surface of the support as known in the art at specific locations (e.g. in specific wells of a plate), and thus are differentiable and may be identified by their location on the support.

After lysing the cells, a buffer that contains a sulfate or sulfonate detergent (preferably in a concentration of 1–10 mM) is added. The detergent is preferably SDS (sodium dodecyl sulfonate); however analogous detergents such as alkyl sulfates or alkane sulfonates may be used. The sample is then contacted with the immobilized primary antibodies under mild denaturation conditions (for instance, the above amount of SDS, a temperature of between about 4 and about 37° C., and for a time of from about 2 to about 72 hours). U.S. Pat. No. 4,658,022 describes a prior art protein assay of this general type (but used only for determination of individual proteins) in which the denaturation of the proteins is conducted at higher temperatures (above 50° C.) and for shorter times (one minute or less). According to that patent, denaturation of proteins in general can enable better detection of proteins, particularly those where the target epitope is hidden. Furthermore, that patent states that denaturation at higher temperature is advantageous because it can be done quickly, thus shortening the overall procedure. However, we have found that denaturation under such conditions is detrimental to obtaining a proper determination of proteins in a process for the simultaneous determination of multiple proteins, such as this invention.

Consequently, in the process of this invention, mild denaturation, as defined herein, is used. In that connection, it should be noted that the fact that a detergent such as SDS would be useful in mild denaturation is surprising. SDS is generally a strong detergent that can potentially denature both the target protein and the capturing antibodies. For instance, SDS can partially denature the antibodies so as to render them non-specific, making it possible for them to bind to other targets than the desired protein. For that reason its use is generally avoided in protein sandwich assays.

The denaturation process itself constitutes another aspect of this invention, and may be used in this process or in another process for simultaneous assay of multiple modified proteins in a sample.

Following the mild denaturation and binding of primary antibodies to the modified proteins, the material is then contacted with one or more second antibodies that are specific to, and bind to, the modified portion of proteins in the sample. The second antibodies may on the one hand be chosen from antibodies that are each specific to a certain modified protein for which detection or determination is sought, for instance, a modified Erk2, JNK or Akt. In that case a multiplicity of such second antibodies is utilized so as to enable a simultaneous detection and/or determination of a multiplicity of such proteins.

In another embodiment, however, the second antibody or antibodies are chosen from those that are specific to a class or subclass of modified proteins. By "class" is meant a type of protein modified at any position or positions, any number of times, by a modifying group. Such classes include, for instance, phosphorylated, glycosylated, ubiquinated, methylated, acetylated or prenylated proteins in general.

The term "subclasses" is meant to refer to a subgroup of such a class, in which the modification occurs at a certain position or, more typically, on a certain amino acid, irrespective of its position or positions in the protein. The subclass is not limited to any specific unmodified protein. Examples of subclasses of phosphorylated proteins, for instance, include phosphotyrosines, phosphoserines, and phosphothreonines. In the case of phosphorylated proteins, the second antibody is preferably a biotinylated-antibody.

Examples of second antibodies for specific modified proteins include, for instance, rabbit monoclonal Anti-phospho-ERK2 (Cell Signaling Technology) and Anti-phospho Lck (BioSources) (phosphorylation).

Second antibodies that are specific to a subclass of proteins include, for instance, antiphosphortyrosine (SIGMA Chemical, clone PT66 cat 3 B1531 or Transduction Lab, Clone PY20—cat # P11123), acetylated-lysine polyclonal antibody (Daiichi) (acetylation), rabbit anti-ubiquitin antibodies (Institute Pasteur) (ubiquination) and mouse monoclonal anti-methylated arginine (Abcam) (methylation).

Use of a second antibody that is specific to a class of proteins, i.e. to phosphorylated or ubiquinated proteins, enables simultaneous determination of multiple modified proteins of that class using a single second antibody. In a further embodiment, a plurality of such second antibodies is utilized, each being selective to a different class of modified proteins. That is, a mixture of second antibodies is used, one (or more) of which is selective to phosphorylated proteins, another to ubiquitins, another to methylated proteins, etc. This enables detection and/or (quantitative) determination of modified proteins in general in a sample, or of several classes of modified proteins, according to the second antibodies that are used.

In the case of phosphorylated proteins, presently available antibodies selective to this class tend to be less accurate than desired. Consequently, if the aim of the assay is to detect or determine modified phosphorylated proteins in general, a combination of antibodies for subclasses, i.e. antibodies to phosphorylation on serine, threonine and tyrosine would be used in preference to a single antibody for the class as a whole.

Antibodies selective to acetylated proteins include those selective to specific acetylated proteins and those that detect selective to acetylated lysine resides in general (i.e. are class-selective for acetylation). Antibodies selective to glycosylated proteins include those selective to specific glycosylated proteins and biotinylated lectin, which is selective to the class of glycosylated proteins.

Those familiar with the art will recognize that binding of analytes to antibodies is influenced by incubation conditions such as time, temperature, pH, ionic strength of reagents, and the like, and the conditions of a given assay will be chosen as known in the art to optimize the sensitivity and specificity of the test and generally suit the ease of use of the protocol and its adaptability to automation.

After contact with the second antibody or mixture of antibodies, the "sandwiched" materials may then be detected and/or quantitatively determined, for instance by contact with a labeled moiety having a component which binds to the second antibodies, such as streptavidin, and which is labeled with phycoerythrin (PE) or with another label, which may be a dye or other type of label such as a radioactive label and determination of the latter using standard techniques. In some instances the detection may be carried out by directly binding the labeled moiety to the second antibodies.

Covalent attachment of fluorescent labels to streptavidin may be effected by a variety of techniques previously described in patent and scientific literature (Haugland, R. P., Bhalagat, M. K., Preparation of avidin conjugates, Methods Mol. Biol. 1998; 80:185–96). Typical fluorescent moieties are described in Chapter 3 of the Manual of Clinical Laboratory Immunology, supra. Alternatively the conjugates may be obtained from a commercial sources. Fluorescent dyes such as fluorescein, the arylsulfonate cyanine dyes, phycobiliprotein dyes, bodipy dyes and the like, may be used. If the particle subsets are distinguished from one another on the basis of incorporation of fluorochromes, then the dyes used in the labeled moieties are selected so as to have fluorescent emissions that are distinct from, and do not interfere with, the emission spectra of the particle subsets. A preferred type of fluorescent material is a class of compounds known as phycobiliproteins, more particularly the phycoerytherins, the phycocyanins, and the allophycocyanins, most preferably the phycoerytherins.

The materials are incubated under appropriate conditions for binding of the streptavidin to the second antibodies. In this overall process, the fluorescently labeled streptavidin binds to the particles through the primary and second antibodies, and through the binding of primary antibodies to the modified proteins. The modified proteins thus can be detected and measured by application of excitation energy having a wavelength selected to excite the chosen fluorescent label, where the emission spectra that is generated is distinct from the emission spectra incorporated in the particles.

Detection of the modified proteins alternatively may be carried out without the use of a label, for instance by use of SPR (Surface-Plasmon Resonance) technology.

By using the methods and kits of this invention, simultaneous determination of a multiplicity of modified proteins in a sample can be carried out. The process is capable of simultaneously detecting and/or determining as many as 100 or more modified proteins in a single sample, using as few as 50 cells. It should be noted, however, that the cell concentration should be about 0.2–900 μg/ml.

In order to prevent the dephosphorylation of proteins by phosphatase, a phosphatase inhibitor, such as NaF or $Na_3VO_4$, should be present during the overall process, from capturing through detection steps.

Another aspect of this invention is a kit for carrying out the process. The kit comprises:
  (a) a plurality of first antibodies, each capable of binding to a specific target protein, each first antibody being immobilized on a solid support material and each first antibody being differentiable from others by a differentiation parameter;
  (b) one or more buffers for lysing and for washing cellular material samples to be assayed
  (c) an assay buffer for conducting the assay, said buffer containing from about 3–10 mM of a sulfate or sulfonate detergent; and
  (d) one or more second antibodies specific to modified proteins, i.e., either to classes or subclasses of modified proteins or to specific individual modified proteins.

As described above, the primary antibodies may either be bound to a plurality of differentiable beads or immobilized at different locations on a solid surface or device such as a chip, slide or plate.

The kit may have additional components, as described below, including the labeled moiety for detecting and/or determining the modified proteins.

EXAMPLE 1

The following represents an example of a kit of this invention, and of a process for simultaneously determining multiple phosphorylated proteins in a sample.

A kit is prepared containing the following:
Phosphoprotein Assay (Detection Modules)
Capturing antibody-conjugated beads (50×, 250 μl)
  (Each analyte=$2.5 \times 10^6$ beads/mL)

Phosphoprotein Detection Antibody (antiphosphortyrosine from SIGMA Chemical—clone PY54)
  50× for Premixed Multi-Plex Assays (120 μl)
  100× for Unmixed Multi-Plex Assays (70 μl each analyte)
  (each Detection Antibody=0.2 mg/mL)
Positive Controls for phospho-JNK and phospho-p38MAPK
  (250 μl/vial at 200 μg/ml)
Positive control for phosphoproteins (250 μl/vial at 200 μg/ml, per protein).
Negative control (250 μl/vial at 200 μg/ml protein)
  Cell Lysis Kit A
Cell Wash Buffer A (1×, 150 ml) (20 mM Tris-HCl, pH 7.35–7.45, 0.9% NaCl)
Cell Lysis Buffer A (1×, 25 ml) (20 mM Tris-HCl, pH 7.8–8.2, 50–500 mM NaCl, 50–100 mM NaF, 0.02–0.08% $NaN_3$, 0.5–3% NP40 or TritonX-100, 4–8 mM EDTA)
Cell Lysis Buffer A, Factor 1 (250×, 100 μl) (500–1000 mM $Na_3VO_4$)
Cell Lysis Buffer A, Factor 2 (500×, 50 μl) (1–2 mg/ml Leupeptin)

It should be noted that the cell wash and cell lysis buffers do not contain SDS or any other sulfate or sulfonate detergent.
  Reagent Kit B
Assay Buffer B (1×, 10 ml) (20 mM Tris-HCl, pH 7.8–8.2, 50–500 mM NaCl, 50 mM NaF, 0.5–3% SDS, 0.02–0.08% $NaN_3$)
Wash Buffer B (1×, 150 ml)

Detection Antibody Diluent B (1×, 10 ml)
Bead Resuspension Buffer B (1×, 40 ml)
Streptavidin-PE (100×, 70 μl)
Filter Plate (96-well)
Adhesive Plate Sealers
Phosphoprotein Assay Instruction Manual Additional Items The following additional items are not necessarily provided with such a kit, but are recommended in using the kit to conduct the process. These items are available from Bio-Rad, Hercules, Calif.

Bio-Plex Protein Array System
Bio-Rad catalog #171-000001, 171-000003, or 171-000005

Bio-Plex Protein Array System Accessories
Bio-Plex validation kit, Bio-Rad catalog #171-203000
Bio-Plex calibration kit, Bio-Rad catalog #171-203060

Bio-Rad DC Protein Assay Kit II
Bio-Rad catalog #500-0112 (with BSA standard)

Cell Lysate Preparation for Adherent Cells

Note that optimal performance of this particular phosphoprotein assay calls for 150 μl of cell lysate (protein concentrate, 300–900 μg/ml) per well. An addition of 2 mM PMSF (phenylmethylsulfonyl fluoride) in the cell lysis buffer is also required. To prepare a 250× stock solution (500 mM PMSF), dissolve 0.436 g PMSF in 5 ml DMSO, aliquot to 0.2–0.5 ml per tube and store at −20° C.

The cells are cultured in a 96-well culture plate or other suitable culture vessel. The final cell lysis buffer is prepared by adding Factors 1 and 2 and a solution of 500 mM PMSF in DMSO to the Cell Lysis Buffer A, but no more than 5–10 minutes prior to lysing the cells. (For a total of 10 ml final cell lysis buffer, add 40 μl of Factor 1, 20 μl of Factor 2 and 40 μl of 500 mM PMSF to 9.9 ml of 1× Cell Lysis Buffer A. Mix well by vortexing.) Then, the reaction is stopped by quickly rinsing the cells with 200 μl 1× Cell Wash Buffer A after aspirating the culture medium.

Lysis buffer is then immediately added to each well or culture vessel. The amount of cell lysis buffer added depends on the cell concentration in each well. The plate is placed on ice. Pipetting is carried out up and down for 5 times with a multi-channel pipette set at 50 μl, followed by agitation of the plate on a plate shaker at 300 rpm for 20 min at 4° C. (For other types of culturing vessels, the vessel is kept on ice and the cell monolayer scraped with a cell scraper; the lysate is transferred to a 15-ml centrifuge tube then rotated end-over-end for 20 min at 4° C.)

Cellular debris is then removed, for example, by centrifugation at 2,000 g for 30 min or 4500 g for 15 min at 4° C. The supernatants are collected for the assay. If the assay is not performed immediately, the cell lysates should be stored frozen at −70 C.

Cell Lysate Preparation for Suspension Cells

The cells are cultured and treated as above. The reaction is stopped and the materials centrifuged at 300 g for 5 min at 4° C. During the centrifugation, the cell lysis buffer is prepared as above. The supernatant is aspirated, and the ice-cold lysis buffer is immediately added to each well or culture vessel. The amount of lysis buffer added depends on the cell concentration in each well. The plate is placed on ice, pipetted and agitated as above; cellular debris is removed and the supernatants collected for the assay as above.

Assay Procedure for Premixed Multi-Plex Assays

Capturing Antibody-Conjugated Beads (Premixed)

If using a 96-well plate, any section not being used should be sealed with an adhesive sealer. The premixed capturing antibody-conjugated beads (25×) are vortex mixed vigorously for 30 seconds, then diluted to a 1× concentration using Wash Buffer B. Each well requires 50 μL of 1× capturing antibody conjugated beads (i.e. 1 μL of capturing antibody conjugated beads (50×)) and 49 μL of 1× Wash Buffer B.

Assay Procedure (Pre-Mixed)

Capturing antibody-conjugated beads (1×) are prepared as directed above. The Assay Buffer B is brought up to room temperature or alternately to 37° C. prior to use and vortex mixed to make sure all components are well dissolved. The cell lysate samples are thawed on ice if they have been stored frozen. Then the apparatus is calibrated (a suitable apparatus for conducting the assay is the Millipore Multi-Screen® Separations System).

The desired number of wells of a 96-well filter plate is pre-wet with 100 μL of 1× Wash Buffer B. The filter plate is placed on a calibrated filter plate vacuum manifold. and the buffer is removed by vacuum filtration. The removal of buffer is carried out between steps of the overall assay procedure, per common practice.

The 1× capturing antibody conjugated beads are vortex mixed for 15 seconds and 50 μL added to each well. 100 μL of the 1× Wash Buffer B is added to each well. 50 μL of positive controls and the negative control are added to the well designated for controls. (The positive and negative cell lysate controls are premixed with 1× Assay Buffer B.)

Then, 25 μL of 1× Assay Buffer B is added per well (except for the controls). 25 μL of unknown cell lysate samples is added; the plate is sealed and covered and shaken overnight at room temperature. The 1× detection antibody mix is prepared 5–10 minutes before the next step. Premixed Phospho-Protein Detection Antibody (50×) is diluted to a 1× concentration with 1×Detection Antibody Diluent B. The total volume of 1× Phospho-Protein Detection Antibody required is based on the number of wells used, allowing for 50 μL per well. The sealing tape is then removed from the plate, and the buffer is removed by vacuum filtration. The plate is washed with 1× Wash Buffer B, with removal of buffer.

The detection antibody is vortex mixed gently and 50 μL added to each well. The plate is sealed and covered, than shaken at room temperature.

The Streptavidin-PE conjugate (100×) is then diluted to a 1× concentration with 1× Wash Buffer B, 5–10 minutes prior to use. The plate is washed and unsealed and buffer is removed. The 1× Streptavidin-PE conjugate is vortex mixed vigorously and 50 μL is added to each well. The plate is covered and sealed, then shaken; then uncovered and washed as before.

The beads in each well are resuspended with 125 μL 1× Bead Resuspension Buffer B. Determination of the content of modified proteins is done using a Bio-Plex System (available from Bio-Rad), a specialized microtiter plate reader.

EXAMPLE 2

Assay for Multiple Modified Proteins

The above procedure was used to simultaneously analyze a sample of cell lysates containing five phosphorylated proteins: phosphorylated p38MAPK, IκBα, Erk2, JNK and Akt1. The proteins were phosphorylated at the following sites: p38MAPK-Thr$^{180}$, Tyr$^{182}$; IκBα-Ser$^{32}$, Ser$^{36}$; Erk2-Thr$^{202}$, Tyr$^{204}$; JNK-Thr$^{183}$, Tyr$^{185}$; Akt1-Ser$^{473}$. Cell lysates were HeLa and HEK-293 simulated with UV, EGF, Fetal Bovine Serum (FBS) or TNF-alpha. The uninduced HeLa cell lysate was also prepared and used as a negative control. All procedures were done on a 96-well filter plate. The cell lysate samples were analyzed by the above procedure and verified for expression of phosphorylated proteins via Western blotting. The result demonstrates: (1) a simultaneous detection of all five phosphorylated proteins above; (2) only 5–10 μg of cell lysate per well was needed for the analysis; (3) an inter-plate and intra-plate coefficient of variation less than 10% and (4) a tight quantitative and qualitative correlation with Western blotting data.

For example, in the detection of phosphorylated IκBα, the above assay detected the expression of phospho-IkB in HeLa cell lysate that was stimulated with TNF-alpha and not in HEK293 stimulated UV, EGF or FBS. The Western blot probe for IκBα also showed a strong band in TNF-alpha stimulated HeLa cell lysate and no visible bands for all other stimulated HEK cell lysates. In another experiment, a dilution of phospho-Erk stimulated cell lysate ranging from 50–5000 ng per analysis was assayed using the above procedure and by Western blot. The increasing band signal of phospho-Erk was observed with increasing concentration of cell lysate. Similarly, the signal for the assay according to this invention also increased with increasing cell lysate concentration. As shown in FIG. 1, when the signals derived from Western blotting (x-axis) and the above assay for multiple modified proteins (y-axis), were plotted and linear curve-fitted, a correlation coefficient ($R^2$) of 0.9804 was obtained. This demonstrates a tight quantitative correlation between the results obtained from (prior art) Western blotting for a single modified protein and those obtained using the novel multiplex analysis of the invention.

What is claimed is:

1. A method for simultaneous detection and/or determination of a plurality of modified proteins in a sample, comprising:
   a) adding a sulfate or sulfonate detergent, in a concentration of about 1–10 mM and a plurality of first antibodies capable of binding to a specific target protein to said sample to create a mixture and incubating at a temperature of between about 4 and 37 degrees Celsius, and for a time of from about 2 to about 72 hours, wherein the first antibodies are immobilized on solid support material, each first antibody being differentiable from others by a differentiation parameter, whereby the first antibodies bind to respective target proteins present in the sample;
   b) removing unbound materials from the locus of the first antibodies;
   c) contacting the materials from step (b) with one or more second antibodies, each of which is specific to a class or subclass of modified proteins or with a plurality of second antibodies, each of which is specific to a modified protein, so as to bind the second antibody or antibodies to modified proteins in the sample; and
   d) detecting and/or determining a plurality of modified proteins in the sample.

2. A method according to claim 1, wherein up to 100 modified proteins are detected and/or determined.

3. A method according to claim 1 wherein the modified proteins are selected from phosphorylated proteins, glycosylated proteins, acetylated proteins, methylated proteins, ubiquinated proteins, and prenylated proteins.

4. A method according to claim 3 wherein the modified proteins are phosphorylated proteins.

5. A method according to claim 1 wherein the solid support material comprises a series of subsets of solid particles, each subset being distinguishable from other subsets in accordance with a particular property or characteristic.

6. A method according to claim 5 in which the solid particles are differentiable by specific color or emission spectra.

7. A method according to claim 5 in which the solid particles comprise spherical particles formed from non-porous glass, polystyrene or latex.

8. A method according to claim 1 in which the solid support material is a microchip, a plate having a multiplicity of wells, or a slide.

9. A method according to claim 1 wherein the materials from step (b) are contacted in step (c) with one or more second antibodies, each of which is specific to a class of modified proteins.

10. A method according to claim 9 in which the materials from step (b) are contacted in step (c) with a second antibody that is specific to a class of modified proteins.

11. A method according to claim 1 in which the materials from step (b) are contacted in step (c) with a second antibody that is specific to a subclass of modified proteins.

12. A method according to claim 1 in which the materials from step (b) are contacted in step (c) with one or more second antibodies specific to phosphorylated proteins.

13. A method according to claim 1 in which the materials from step (b) are contacted in step (c) with a plurality of second antibodies, each of which is specific to a modified protein.

14. A method according to claim 1 in which the materials from step (b) are contacted in step (c) with a plurality of second antibodies, each of which is specific to a phosphorylated protein.

15. A method according to claim 14 in which the proteins are selected from phosphorylated p38MAPK, phosphorylated IÿB, phosphorylated Erk2, phosphorylated JNK and phosphorylated Akt.

16. A method according to claim 1 in which the second antibodies are biotinylated antibodies.

17. A method according to claim 1 in which the modified proteins are detected and/or determined in step (d) by contacting the product of step (c) with a labeled moiety.

18. A method according to claim 17 in which the labeled moiety comprises a phycobiliprotein.

19. A method according to claim 17 in which the labeled moiety comprises a phycoerythrin.

20. A method according to claim 17 in which the labeled moiety comprises a conjugate of a labeled moiety with streptavidin.

21. A method according to claim 1 in which the sample is a cell lysate.

22. A method according to claim 1 in which the detergent is sodium dodecyl sulfate.

23. In a process for simultaneously analyzing a sample for a plurality of modified proteins, comprising denaturing a plurality of modified proteins, wherein the improvement comprising adding a sulfate or sulfonate detergent, in a concentration of about 1–10 mM and a plurality of first antibodies capable of binding to a specific target protein to said sample to create a mixture and incubating at a temperature of between about 4 and 37 degrees Celsius, and for a time of from about 2 to about 72 hours.

24. A process according to claim 23 in which the detergent is sodium dodecyl sulfate.

* * * * *